United States Patent [19]
Jacobs

[11] Patent Number: 5,314,919
[45] Date of Patent: May 24, 1994

[54] CALCIUM SUPPLEMENTS
[75] Inventor: Stephen A. Jacobs, Fairfield, Ohio
[73] Assignee: The Procter & Gamble Company, Cincinnati, Ohio
[21] Appl. No.: 652,386
[22] Filed: Feb. 6, 1991

Related U.S. Application Data

[63] Continuation of Ser. No. 515,529, Apr. 26, 1990, abandoned, which is a continuation of Ser. No. 408,453, Sep. 14, 1989, abandoned, which is a continuation of Ser. No. 90,813, Aug. 28, 1987, abandoned.

[51] Int. Cl.⁵ .................. A61K 31/19; C07C 59/245
[52] U.S. Cl. ..................................... 514/574; 562/582
[58] Field of Search .................... 562/582; 514/574

[56] References Cited

U.S. PATENT DOCUMENTS 4,551,342 11/1985 Nakel et al. ...................... 426/548
4,722,847 2/1988 Heckert ............................. 426/74

FOREIGN PATENT DOCUMENTS 4384M 10/1966 France .
2219778 9/1974 France .
548767 1/1979 Japan .
97248 8/1981 Japan ................................. 562/582
161239 7/1986 Japan ................................. 562/582
193065 1/1938 Switzerland .

OTHER PUBLICATIONS

L. Nilas et al., "Calcium Supplementation and Postmenopausal Bone Loss", 289 *British Medical Journal* 1103 (1984).
Spencer et al., "NIH Consensus Conference: Osteoporosis–Factors Contributing to Osteoporosis", 116 *J. Nutrition* 316 (1986).

*Primary Examiner*—José G. Dees
*Assistant Examiner*—Joseph M. Conrad
*Attorney, Agent, or Firm*—David L. Suter

[57] ABSTRACT

A calcium citrate malate complex or mixture having a molar composition of calcium:citrate:malate of about 6:2:3. The calcium citrate malate is preferably administered in an oral dosage form, containing pharmaceutically-acceptable carriers and excipients.

7 Claims, No Drawings

CALCIUM SUPPLEMENTS

This is a continuation of application Ser. No. 07/515,529, filed Apr. 26, 1990, now abandoned, which was a continuation of application Ser. No. 07/408,453, filed Sep. 14, 1989, abandoned, which was a continuation of application Ser. No. 07/090,813, filed on Aug. 28, 1987, abandoned.

BACKGROUND OF THE INVENTION

This invention relates to a novel material and composition useful as a calcium supplement for humans and other animals. In particular, this invention relates to specific calcium citrate malate materials and dosage forms containing such materials.

Calcium is the fifth most abundant element in the human body. It plays an important role in many physiological processes, including nerve and muscle functions. Not surprisingly, nutritional and metabolic deficiencies of calcium can have broad-ranging adverse effects. Since about 90% of the body's calcium is found in bone tissues, many of these adverse effects are manifested through deficiencies in the structure, function and integrity of the skeletal system.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is idiopathic "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the wrist and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling occurs in a series of discrete pockets of activity in the bone, called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

In a healthy adult, the rate at which the osteoclasts and osteoblasts are formed maintains a balance of bone resorption and bone formation. However, in osteoporotics an imbalance in this remodeling process develops, resulting in loss of bone at a rate faster than the accretion of bone. This imbalance is much more severe, and occurs at a younger age, in osteoporotics as compared to healthy adults.

Many compositions and methods are described in the medical literature for the "treatment" of osteoporosis. Many of these compositions and methods attempt to either slow the loss of bone or to produce a net gain in bone mass. See, for example, R. C. Haynes, Jr. et al., "Agents affecting Calcification", *The Pharmacological Basis of Therapeutics*, 7th Edition (A. G. Gilman, L. S. Goodman et al. , Editors, 1985) ; and G. D. Whedon et al., "An Analysis of Current Concepts and Research Interest in Osteoporosis", *Current Advances in Skeletogenesis* (A. Ornoy et al., Editors, 1985). Estrogen is often used to affect the metabolism of calcium. Treatments using fluoride have also been described. However, the utility of such agents may be limited, due to possible adverse side effects. See W. A. Peck, et al., *Physician's Resource Manual on Osteoporosis* (1987), published by the National Osteoporosis Foundation (incorporated by reference herein).

Nutritional therapies for osteoporosis have also been proposed. Many calcium-containing compounds and compositions have been described for use as nutritional supplements. Many commercial preparations are also available, typically containing calcium carbonate. Calcium chloride, calcium gluceptate, calcium gluconate, calcium lactate, calcium phosphate, calcium citrate, and other calcium salts have also been described for use in calcium supplements. The use of calcium citrate, for example, is described in French Patent 2,219,778, Monteau, published Sep. 27, 1974; and World Patent Publications 86/04814 and 86/04815, Pak et al., both published Aug. 28, 1986. Food supplements containing calcium citrate malate are described in Japanese Patent Document 56/97, 248, Kawai, published Aug. 5, 1981.

The utility of these known supplements varies. Unlike agents (such as estrogen) which affect the metabolism of bone, calcium nutritional supplements have been thought to merely provide a source for calcium (which may or may not be properly absorbed and metabolized). Indeed, the literature is bereft of any credible clinical data supporting the utility of any of these calcium supplements to actually treat osteoporosis (to actually build bone). See, for example, B. Riis et al., "Does Calcium Supplementation Prevent Postmenopausal Bone Loss?", 316 *New England J. of Medicine* 173-177 (1987); L. Nilas et al., "Calcium Supplementation and Postmenopausal Bone Loss", 289 *British Medical Journal* 1103-1106 (1984); and H. Spencer et al., "NIH Consensus Conference: Osteoporosis", 116 *Journal of Nutrition* 316-319 (1986).

It has now been discovered, however, that certain calcium citrate malate materials are highly efficacious calcium supplements, providing increased absorption and bioavailability compared to calcium supplements known in the art. In particular, as compared to calcium supplements known in the art, these methods afford greater efficacy in the treatment of osteoporosis and related disorders.

SUMMARY OF THE INVENTION

The present invention provides a calcium citrate malate complex or mixture having a molar composition of calcium:citrate:malate of about 6:2:3. The calcium citrate malate is preferably administered in an oral dosage form, containing pharmaceutically-acceptable carriers and excipients.

DESCRIPTION OF THE INVENTION

The present invention encompasses a calcium citrate malate, dose forms, and methods of administration of the calcium citrate malate to a human or other animal subject. Specific compounds and compositions to be used in the invention must, accordingly, be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

Calcium Citrate Malate and Compositions

This invention provides a mixture of calcium salts, herein "calcium citrate malate", comprising calcium salts of citric acid and malic acid, having a molar ratio of calcium:citrate:malate of about 6:2:3. The calcium citrate malate may consist of a mixture of calcium citrate and calcium malate, a complex of calcium containing citrate and malate ligands, a mixture of a calcium salt with citric acid and malic acid, or combinations thereof. (Mixtures of calcium salt and citric and malic acids may be used to form calcium citrate malate in situ, in a liquid dose form, or in the acid environment of the stomach of the subject to whom the mixture is administered.)

The calcium citrate malate for use in the methods of this invention may be provided in solid or liquid dosage forms (herein "calcium supplements"). Calcium citrate malate for use in solid forms may be made, for example, by first dissolving citric acid and malic acid, in the desired molar ratio, in water. Calcium carbonate may then be added to the solution, in such amount that the ratio of moles calcium to moles citrate and moles malate is as desired. Carbon dioxide will be evolved. The solution may then be dried (as by freeze drying or oven drying) to obtain the calcium citrate malate. The calcium citrate malate made in such commercial processes may, of course, vary from a precise 6:2:3 molar composition. Such commercial calcium citrate malate may contain, therefore, other anions such as (for example) carbonate, hydroxide, and mixtures thereof.

Various oral dosage forms of calcium citrate malate may be used in the present invention. Such dosage forms comprise a safe and effective amount of a calcium citrate malate of this invention and a pharmaceutically-acceptable carrier. Preferably the pharmaceutically-acceptable carrier is present at a level of from about 0.1% to about 99%, preferably from about 0.1% to about 75%, by weight of the composition. Unit dosage forms (i.e., compositions containing an amount of calcium citrate malate suitable for administration in one single dose, according to sound medical practice) preferably contain from about 425 mg (milligrams) to about 4300 mg of calcium citrate malate, corresponding to from about 100 mg to about 1000 mg of calcium (on an elemental basis). Preferably, the unit dosage forms of this invention contain from about 425 mg to about 2100 mg, more preferably from about 850 mg to about 1300 mg of calcium citrate malate.

Solid dosage forms include tablets, capsules, granules and bulk powders. Aside from the calcium citrate malate, tablets may contain, as carriers (for example), suitable binders, lubricants, diluents, disintegrating agents, coloring agents, flavoring agents, flow-inducing agents, melting agents, and mixtures thereof. Liquid oral dosage forms include aqueous solutions, emulsions, suspensions, solutions and/or suspensions reconstituted from non-effervescent granules and effervescent preparations reconstituted from effervescent granules. Such oral dosage forms may contain, as carriers (for example), suitable solvents, preservatives, emulsifying agents, suspending agents, diluents, sweeteners, melting agents, coloring agents, flavoring agents, and mixtures thereof.

Specific examples of pharmaceutically-acceptable carriers and excipients that may be used to formulate oral dosage forms of the present invention are described in U.S. Pat. No. 3,903,297, Robert, issued Sep. 2, 1975, incorporated by reference herein. Techniques and compositions for making dosage forms useful in the methods of this invention are described in the following references, all incorporated by reference herein: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2d Edition. (1976).

Methods of Use

The present invention also provides methods for the administration of a calcium supplement to a human or other animal subject in need thereof, comprising administering to said subject a safe and effective amount of the calcium citrate malate of this invention. Preferably, from about 750 mg to about 8600 mg of calcium citrate malate are administered to said subject, per day, corresponding to from about 175 mg to abut 2000 mg of calcium (on an elemental basis). More preferably, from about 1000 mg to about 6400 mg, more preferably from about 2100 mg to about 4300 mg of calcium citrate malate are administered, per day. "Administering" refers to any method which, in sound medical practice, delivers the calcium citrate malate used in this invention to the subject to be treated in such a manner so as to be effective in the building of bone. Preferably, the calcium citrate malate is administered orally.

The specific period of time for which the calcium citrate malate is to be administered may depend upon a variety of factors. Such factors include, for example, the amount of calcium citrate malate employed, the specific condition to be treated, the age and sex of the subject, the nutritional habits of the individual, and the general health of the individual (including the presence of other disorders). The methods of this invention may be employed in the treatment or prevention of any of a variety of disorders. Thus, preferably, the methods of this invention are employed on a "subject" that is "in need" of treatment or prevention of such disorders, according to sound medical practice. The calcium citrate malate and the calcium supplements of this invention may be used to replace or supplement other dietary sources of calcium for humans or other animals. The calcium citrate malate and supplements may be used to assure adequate intake of calcium for metabolic needs, or to prevent or treat certain disorders. The use of calcium citrate malate materials for the building of bone (e.g., for the treatment of osteoporosis) is described in copending U.S. patent application Ser. No. 07/590,314, Kochanowski, "Methods for the Treatment of Osteoporosis and Related Disorders", filed Aug. 28, 1987 (incorporated by reference herein).

A preferred method of this invention is for the treatment of osteoporosis. Such methods may include administration of calcium citrate malate alone, or in combination with other therapeutic agents. In particular, one method of this invention involves administration of calcium citrate malate as part of an "ADFR" regimen. Such a regimen, in general, comprises administration to the subject of a bone-cell activation agent (such as an inorganic phosphate); followed by administration of an osteoclasts depressant, to inhibit bone resorption (such as a diphosphonate); followed by a "free" period during which osteoblast bone formation occurs. The entire cycle is preferably repeated. Such regimens, among those useful herein, are described in Belgian Patent Publication 902,307, Anderson et al., "Treatment of Osteoporosis", published Oct. 29, 1985 (incorporated by reference herein) and Belgian Patent Publication 902,308, Flora, "Treatment of Osteoporosis", published Oct. 29, 1985 (incorporated by reference herein). Preferably, in such regimens calcium citrate malate is administered during the free period. Kits to facilitate ADFR regimens are described in European Patent Specification 162,510, Uchtman, "Kit for Use in the Treatment of Osteoporosis", published Nov. 27, 1985 (incorporated by reference herein).

Another method of this invention involves administration of calcium citrate malate as part of a regimen comprising intermittent dosing of certain polyphosphonate compounds. Such methods comprise administration of the polyphosphonate followed by a "rest period". Such regimens, among those useful herein, are described in European Patent Specification 210,728, Flora et al., "Regimen for Treating Osteoporosis", published Feb. 4, 1987 (incorporated by reference herein). Preferably, calcium citrate malate is administered during the rest period.

The following non-limiting examples illustrate the compositions, processes and uses of the present invention.

EXAMPLE I

A composition is prepared containing calcium citrate malate having a molar calcium:citrate:malate composition of about 6:2:3. The calcium citrate malate is made by first dissolving approximately 384.2 grams of citric acid and approximately 402.3 grams of malic acid in approximately 2 liters of water. This citrate/malate solution is then heated to approximately 55° C. (131° F.), with stirring. Separately, approximately 600.6 grams of calcium carbonate is added to approximately 1.2 liters of water, forming a slurry, with stirring.

The citrate/malate solution is then removed from its heat source, and the calcium carbonate slurry is added slowly, with stirring. The rate of addition is controlled, to contain the reaction as carbon dioxide is released. An additional quantity of water, approximately 0.4 liters, is finally added. The reaction mixture is then stirred for approximately 1 to 1.5 hours. The reaction is essentially complete as the pH of the solution equilibrates to approximately 4.3.

A precipitate of calcium citrate malate is thus formed. The excess reaction liquid is filtered off. The calcium citrate malate is dried, for approximately 12 hours, at approximately 105° C. (221° F.), reducing the moisture level to less than about 1%. The dried product is then milled to approximately 10–20 mesh size, for a swallowable tablet formulation.

The swallowable tablet dosage form is then made, comprising:

| Component | % (by weight) |
| --- | --- |
| calcium citrate malate* | 99.73 |
| magnesium stearate | 0.27 |

*having a molar calcium:citrate:malate composition of approximately 6:2:3, made as described above in this Example.

The tablet formulation is made by thoroughly admixing the powders, and tabletting using a standard tablet press, to form tablets weighing approximately 1104 milligrams. The tablets are then coated, using a pan coater. The coating solution contains approximately 11% hydroxypropylmethyl cellulose, approximately 2% polyethylene glycol, approximately 3.5% colorant, and the balance of water.

The composition is administered to an elderly human male subject suffering from osteoporosis. The mass of the subject's thoracic vertebrae is determined by dual-energy photon absorptiometry. The human subject is then administered 4 of the tablets, comprised as above, each day for three months. The mass of the subject's vertebrae is then remeasured, indicating an increase in bone mass.

EXAMPLE II

A human male subject, suffering from secondary osteoporosis as a result of a partial gastrectomy, is treated by a method of this invention. Specifically, a chewable tablet composition is administered to the subject, comprised as set forth below.

| Component | % (by weight) |
| --- | --- |
| calcium citrate malate* | 46.94 |
| mannitol | 46.69 |
| magnesium stearate | 0.68 |
| flavorant | 5.69 |

*having a molar calcium:citrate:malate composition of approximately 6:2:3, made in a manner analogous to that described in Example I, above.

The tablets are made by thoroughly admixing the powders, and tabletting on a standard tablet press, forming tablets weighing approximately 2356 milligrams. Each tablet contains approximately 250 mg of calcium (on an elemental basis). The composition comprised as above, when administered to a pregnant female human, is effective in providing a sufficient quantity of bioavailable calcium.

What is claimed is:

1. Calcium citrate malate, having a molar ratio of calcium:citrate:malate of about 6:2:3.

2. A complex of calcium containing citrate and malate ligands, according to claim 1.

3. A calcium supplement comprising a safe and effective amount of a calcium citrate malate of claim 1, and a pharmaceutically-acceptable carrier.

4. A calcium supplement, according to claim 3, in unit dosage form comprising from about 425 milligrams to about 2100 milligrams of said calcium citrate malate.

5. A calcium supplement, according to claim 3, in solid dosage form wherein said pharmaceutically-acceptable carrier is present at a level of from about 0.1% to about 75%, by weight.

6. A method of administering a calcium supplement to a human or other animal subject in need thereof, comprising administering to said subject a safe and effective amount of a calcium citrate malate of claim 1.

7. A method, according to claim 6, wherein said calcium citrate malate is administered at a level of from about 1000 milligrams to about 6400 milligrams, per day.

* * * * *